United States Patent [19]

Schäfer et al.

[11] Patent Number: 5,011,661
[45] Date of Patent: Apr. 30, 1991

[54] CONTACT LENS CARE SET

[75] Inventors: Horst Schäfer, Aschaffenburg-Obernau; Gerhard Ludwig, Stromberg; Rainer Sunderdiek, Aschaffenburg-Schweinheim, all of Fed. Rep. of Germany

[73] Assignee: Ciba-Geigy Corporation, Ardsley, N.Y.

[21] Appl. No.: 423,654

[22] Filed: Oct. 18, 1989

Related U.S. Application Data

[63] Continuation-in-part of Ser. No. 140,950, Dec. 29, 1987, abandoned, which is a continuation of Ser. No. 883,964, Jul. 10, 1986, abandoned.

[30] Foreign Application Priority Data

Jul. 10, 1985 [DE] Fed. Rep. of Germany ....... 3524659
Sep. 11, 1985 [DE] Fed. Rep. of Germany ....... 3532433

[51] Int. Cl.$^5$ ............... A61K 9/24; A61K 9/58; A61L 2/18
[52] U.S. Cl. ............... 422/30; 134/27; 422/28; 422/292; 422/293; 424/471; 424/482; 514/840
[58] Field of Search ........... 422/28, 30, 292, 293; 134/26-29; 424/468, 471, 472, 474, 475, 482; 514/840

[56] References Cited

U.S. PATENT DOCUMENTS

| | | | |
|---|---|---|---|
| 3,577,512 | 5/1971 | Shepherd et al. | 424/32 |
| 3,912,451 | 10/1975 | Gaglia, Jr. | 422/30 |
| 4,312,833 | 1/1982 | Clough et al. | 422/30 |
| 4,459,279 | 7/1984 | Stricker et al. | 424/32 |
| 4,503,030 | 3/1985 | Edgren et al. | 424/473 |
| 4,568,517 | 2/1986 | Kaspar et al. | 422/30 |
| 4,670,178 | 6/1987 | Huth et al. | 514/840 X |

FOREIGN PATENT DOCUMENTS

| | | | |
|---|---|---|---|
| 0063014 | 10/1982 | European Pat. Off. | 424/31 |
| 0082798 | 6/1983 | European Pat. Off. | 422/30 |
| 124461 | 1/1984 | European Pat. Off. | |
| 139994 | 5/1985 | European Pat. Off. | |
| 147100 | 7/1985 | European Pat. Off. | |
| 8605695 | 10/1986 | PCT Int'l Appl. | |
| 8607264 | 12/1986 | PCT Int'l Appl. | |

Primary Examiner—Robert J. Warden
Assistant Examiner—Jill Johnston
Attorney, Agent, or Firm—Edward McC. Roberts; Irving M. Fishman

[57] ABSTRACT

A method for disinfecting a contact lens comprises immersing the lens in an aqueous solution of $H_2O_2$ having a pH of 4 or below and adding to the solution a neutralizing agent comprising a catalyst for decomposing any residual $H_2O_2$ and a retarding agent for delaying the decomposition of the $H_2O_2$ for a predetermined time in order to permit sterilization of the lens to be substantially complete. The retarding agent preferably comprises either a polymeric coating which dissolves gradually in the $H_2O_2$ solution or a semipermeable membrane enveloping the catalyst. The neutralizing agent preferably also contains an auxiliary material which raises the pH of the acidic $H_2O_2$ solution. The enzymatic decomposing agent can be embedded in a particulate carrier substance forming the bottom part of a two part container, the upper part of which contains an aqueous solution of $H_2O_2$, and the bottom part being separable from the upper part and covered by an inert sieve netting impermeable to the $H_2O_2$ solution but permeable to the decomposing agent.

11 Claims, 2 Drawing Sheets

CONTACT LENS CARE SET

This application is a continuation-in-part of Ser. No. 140,950, filed Dec. 29, 1987, which is a continuation of Ser. No. 883,964, filed Jul. 10, 1986.

The invention relates to a contact lens care set.

Care sets for soft and hard contact lenses serve to clean, to disinfect and to stabilize the optical properties and to improve the wear comfort of the contact lenses. Hydrogen peroxide, as antimicrobial substance, has become more important recently for disinfecting and cleaning contact lenses. Compared to chlorhexidine salts or organomercury compounds, such as thiomersal, which are also used to disinfect contact lenses, hydrogen peroxide has a better antimicrobiological effect, especially with respect to the relatively resistant Aspergillus species. The known hydrogen peroxide solutions, used to clean contact lenses, are 3% peroxide solutions (German Patent No. 2,425,714). After treatment of the contact lenses with these solutions, relatively large residual amounts of hydrogen peroxide solution adhere to the lens. When lenses so treated are inserted, these residual amounts lead to varying degrees of irritation of the mucous membrane. Therefore, after treatment with a hydrogen peroxide solution, it is necessary to treat the lens with a neutralizing solution, by means of which the hydrogen peroxide is split into water and oxygen. The elimination after the sterilization treatment of residual amounts of hydrogen peroxide by decomposition with the help especially of heavy metal catalyst is known from the aforementioned German Patent No. 2,425,714. The use of two different treatment steps is required here, namely, first of all, the treatment step of sterilizing the lens and, after discarding the sterilizing solution, the treatment step of eliminating the residual hydrogen peroxide in an aqueous system containing the catalyst. The handling of the lens during the care and cleaning operations therefore is relatively complicated. The choice of suitable catalysts, which are used for the decomposition of residual amounts of hydrogen peroxide, also presents difficulties.

As catalysts for the decomposition of the hydrogen peroxide, used to disinfect and clean contact lenses, after the cleaning and disinfecting treatments have been carried out, the use of enzymatic peroxidases, especially catalase, is known from the EP-A-82 798. In this case also, however, the hydrogen peroxide solution is poured off after its disinfecting treatment and replaced by a neutralizing solution which contains the peroxide-neutralizing catalyst or catalysts (i.e., peroxidases). Here also, therefore, two different, successive treatment steps are employed, so that the care treatment of the lens remains complicated.

In both cases, a contact lens care treatment simultaneously using hydrogen peroxide and a neutralizing solution with a decomposition catalyst, for example, has been impossible because, in such case, the hydrogen peroxide is decomposed into oxygen and water by the neutralizing solution via its decomposition catalyst, for example, before it can have a sufficient sterilizing action to kill the germs on the lens which requires from about one to about four hours, especially for a soft lens.

SUMMARY OF THE INVENTION

It is, therefore, an object of the invention to provide a contact lens care set which, in one step, keeps hydrogen peroxide active sufficiently long at least for substantially sterilizing the lens and then neutralizes at least residual hydrogen peroxide on the lens at least substantially so that the lens can then be worn, at least generally, without discomfort.

To this and other ends, the invention provides a contact lens care set having at least two agents: hydrogen peroxide and a neutralizing agent. The hydrogen peroxide is sufficient to be effective at least for substantially sterilizing at least one of a hard or soft contact lens and, preferably, either. The neutralizing agent is sufficient to be effective at least for decomposing any residual amount of the hydrogen peroxide on the lens into oxygen and water after the hydrogen peroxide has so sterilized the lens at least substantially, whereby the lens can then be worn, at least generally, without discomfort. The neutralizing agent has at least two constituents: a catalyst or enzyme, preferably for so decomposing the residual hydrogen peroxide, and a retarding agent. The retarding agent delays the time of release of at least so much of the neutralizing agent as decomposes the residual hydrogen peroxide, e.g., the catalyst, into the hydrogen peroxide until the hydrogen peroxide has so sterilizing the lens.

The invention therefore substantially facilitates the care of the contact lens, whether hard or soft, because only a one-step treatment is required. The lens and the neutralizing agent with the catalyst and the retarding agent that controls the time-delayed release of at least part of the neutralizing agent such as the catalyst, for example, are placed into a sterilizing hydrogen peroxide solution. The retarding agent, which comes into contact with the hydrogen peroxide during the immersion, then releases at least the neutralizing portion of the catalyst-containing neutralizing agent after the hydrogen peroxide has acted on the contact lens that is to be treated for a time sufficient for the lens sterilization.

For this, the neutralizing agent may be coated with its retarding agent may be coated with its regarding agent for immersion in the hydrogen peroxide in a water solution with the lens. The delayed release time then can be adjusted (especially up to four hours), for example, by the thickness of the coating which dissolves into the hydrogen peroxide solution. As a result of the release of the catalyst-containing neutralizing agent when the coating dissolves, the neutralizing acts automatically, without further help from the contact-lens wearer taking care of the contact lens, on the hydrogen peroxide solution. The hydrogen peroxide solution is acidic (with a pH of less than 4) in the stable state for effecting both the sterilization and the dissolving. The catalyst, for example, inside the coating then decomposes the sterilizing hydrogen peroxide solution in the treatment container therefor in which the lens to be treated and the neutralizing agent have also been placed at the same time. Examples of the composition of the hydrogen peroxide solution and of the catalyst- or enzyme-containing neutralizing agent are given in the German Offenlegungsschrift 3,410,400.

Moreover, the following composition is suitable as neutralizing agent:

0.05 weight percent catalase concentrate, 260,000 units/mL 0.05 weight percent hydroxypropylmethylcellose USP XX 0.05 weight percent $NaH_2PO_4 \times 2H_2O$ DAB 8

0.25 weight percent $Na_2HPO_4 \times 2H_2O$ 0.75 weight percent sodium chloride EP I The following is a further suitable composition of the neutralizing agent:

3–12 mg suitable buffer substance(s) or mixture, for example, alkali phosphate, borate or citrate, glycine
40–70 mg neutral electrolyte (for example, NaCl, KCl)
5–10 mg alkali hydrogen carbonate
5–10 mg water-soluble polymer, for example, polyvinylpyrrolidone
0.2–1 mg catalyst (catalase, peroxidase)

per single dose.

This amount is sufficient to decompose, to neutralize and to adjust to an osmolarity of 270–320 mosmol 7 mL of an hydrogen peroxide solution. These 7 mL correspond to the volume of a standard contact lens case or contact lens treatment body.

An example of a further special composition of the neutralizing agent is the following:

5.6 mg potassium hydrogen phosphate
8 mg disodium hydrogen phosphate
52.4 mg NaCl
7 mg sodium hydrogen carbonate
4.8 mg polyvinylpyrrolidone K25
0.3 mg catalyst The compositions of the neutralizing agent, given above, can be used as capsule fillings, the capsule being fashioned as the retarding agent, which surrounds the catalyst-containing neutralizing agent. The capsule comprises a water-soluble polymer, especially a polyvinyl alcohol.

The neutralizing agent may also be formed into a tablet, which is provided with a water-soluble coating for the time-delayed dissolution of the tablet. The water-soluble coating may comprise a polymer, soluble in an acidic medium, such as a polymer of dimethylaminomethacrylate and neutral methacrylate esters. The coating may also comprise a pH-neutral, soluble polymer. Polymers, suitable for this purpose, are, for example, soluble cellulose ethers such as methylcellulose, methylhydroxypropylcellulose, methylhydroxyethylcellulose, hydroxypropylcellulose, hydroxyethylcellulose, sodium carboxymethylcelluloses; cellulose acetate phthalate; hydroxypropylmethylmethylcellulose phthalate; polymers of methacrylic acid and methacrylate esters; a coating of an aqueous dispersion of a copolymer of methacrylic acid and methacrylate esters; a coating of an aqueous dispersion of cellulose acetate phthalate; copolymers of methyl vinyl ether and maleic anhydride and polyvinyl alcohols.

Suitable polyalcohols, especially in an amount of 0.2–1 mg/tablet, can be added to these polymers to control the time delay, 1,2-propyleneglycol polyethylene glycols and citrate esters being suitable as polyalcohols.

The coating can be produced from the water-soluble polymer by known processes, for example, by spray-coating a film in the coating pan, by the fluidized bed process (Wurster process) or in closed systems. The preferred amount of polymer, coating a tablet, is 2.0 to 5.0 mg.

The following is an example of a tablet composition, which forms the catalyst-containing neutralizing agent:

11.2 mg disodium hydrogen phosphate
55.8 mg NaCl
4.8 polyvinylpyrrolidone K25
0.2 mg catalyst (catalase, peroxidase)

The following is an example of an acid-soluble polymer, suitable as a coating:

1.9 mg methacrylate ester
0.4 mg hydroxypropylmethylcellulose
0.2 mg polyethylene glycol (1000)

The following is an example of a coating film of a neutral-soluble polymer:

2.2 mg hydroxypropylmethylcellulose phthalate
0.3 mg polyethylene glycol (1000)

It is also possible to seal a catalyst-containing neutralizing agent, which has been formed into a tablet, in a water-soluble film, for example, of polyvinyl alcohol, which acts as a retarding agent. Plasticizers of multihydric alcohols and water are added in an amount of 3.5% to 5% to the polyvinyl alcohol film, as a result of which a time-delayed dissolution of the film is effected. The films may be as thick as 30–150 μm. The gas permeability (DIN 53 380) is 0.9–1.4 $cc/m^2/d/bar$. The films can be welded at temperatures ranging from 140°–190° C. with a contacting pressure of 4–5 bar.

The catalyst-containing neutralizing agent, formed into a tablet, may also be coated with an insoluble, yet semipermeable membrane. This membrane may also be applied by known coating processes, such as spray-coating the film, by the fluidized bed process or in closed systems, and moreover in an amount of 3 to 10 mg/tablet. The semipermeable membrane may be formed, for example, as follows from an organic solution of ethylcellulose, an aqueous dispersion of ethylcellulose, a copolymer of acrylate/methacrylate esters with trimethylammoniummmethacrylate, an aqueous dispersion of mixed methyl methacrylates and ethyl methacrylates; to control the diffusion rate, suitable plasticisers can be added, especially in an amount of 1.0–5.0 mg/tablet. As plasticizer, 1,2-propyleneglycol, polyethylene glycols and citrate esters are suitable. An example of the composition of a semipermeable membrane is as follows:

3.8 mg ethylcellulose N22
1.2 mg polyethylene glycol (6,000)

A further example of a retarding agent, by means of which a time-delayed release of the catalyst, which decomposes hydrogen peroxide, and of the neutralizing agent can be attained, is a swellable, yet sparingly soluble or insoluble matrix, especially in tablet form, in which the catalyst-containing neutralizing agent is distributed. The catalyst-containing neutralizing agent may have one of the aforementioned compositions, which is incorporated in the matrix that may comprise natural or partly synthetic polymers. The matrix, especially in tablet form, can be produce by conventional processes, for example, by granulating and molding the starting materials. It is of course also possible to process the mixture of starting materials directly into tablets without prior granulation. Polymers, suitable for the formation of the matrix, are the soluble cellulose ethers, such as those given by way of example above, the alkali salts of alginic acid, methacrylic acid derivatives, especially acrylate/methacrylate esters, acrylic acid derivatives, dextrans (MW 1,000–75,000) and polyvinyl alcohols. The following is an example of the matrix, in which the catalyst-containing neutralizing agent is incorporated:

0.3 mg catalyst (catalase, peroxidase)
10.2 mg disodium hydrogen phosphate
55.8 mg NaCl
4.7 mg polyvinylpyrrolidone K25
15 mg hydroxypropylmethylcellulose Tablets are molded to have, for example, a weight of 86 mg and a 6 mm round format.

It is also possible to incorporate the components of the catalyst and the neutralizing agent in a highly-concentrated, aqueous polymer solution and, after casting and drying, to produce from this sectile films 1.0–3.0 mm thick. By cutting the film to size, appropriate dosage units can be produced in precalculated superficial dimensions. The water-soluble polymers act as retarding agent, through which the time-delayed release of catalyst and neutralizing agent is attained. Suitable polymers are water-soluble cellulose ethers, like those given above by way of example, alkali alginates, dextrans and polyvinyl alcohols.

It is known in the medical sector concerned with the administration of drugs that therapeutic systems may be used in the form of tablets, semipermeable membranes and matrices, which are brought into a particular target area of a biosystem in order to bring about a constant delivery of drug over a prolonged period of time. In contrast to this, the invention provides that the hydrogen peroxide-decomposing catalyst, together with the sterilizing hydrogen peroxide, can be used simultaneously in the treatment of contact lenses without adverse effect by the catalyst, which decomposes the hydrogen peroxide, on the desired sterilizing action of the hydrogen peroxide over a period of, for example, four hours. The decomposing action of the catalyst on the hydrogen peroxide sets in only at the end of the desired treatment time.

A delayed release of the catalyst can also be achieved by immobilizing the catalyst on particulate carrier substances, especially acrylic resin pellets, for example, by bonding over reactive oxiran groups. The carrier substances, with the catalyst, especially an enzymatic catalyst, immobilized thereon, are disposed in an adequate amount, for example in a bottom part or a lid with screw thread of a contact lens treatment container or a contact lens case and are separated from the treatment solution, which contains the pH-neutralizing materials and the neutral salts together with the hydrogen peroxide, by permeable, inert sieve netting. In this version, the catalyst is disposed in a part of the treatment container without mixing with the treatment solution. By these means the danger is avoided, that the catalyst material will collect or accumulate in the soft lens material during the treatment of soft contact lenses. For example, an amount of carrier substances with an immobilized enzymatic catalyst, sufficient for 30-day repeated use, can be accommodated in the container part.

The treatment solution, in which the release of catalyst-containing neutralizing agent takes place, may have a pH of about 7 to 7.5 and especially of 7.3 and an osmolarity of about 300 mosmol.

A color change, especially the use of a color indicator (pH/redox indicator), changing color at a pH of 7.0 to 7.5 and especially at 7.3, indicates to the user that the hydrogen peroxide, used for sterilizing treatment, has been decomposed. For this purpose, high molecular weight dyes, which do not penetrate into the lens material, are especially suitable.

So that the catalyst, which preferably is an enzymatic catalyst, exerts its action only after the disinfecting or sterilizing treatment of the lens, this catalyst additive, together with auxiliary materials, which are present in the neutralizing agent and which serve to neutralize the hydrogen peroxide, may be packaged in a coating, which ensures that the catalyst for decomposing the hydrogen peroxide is released only after the necessary treatment time (up to four hours). There are a number of possibilities for accomplishing this.

The coating or packing of the catalyst and the auxiliary materials has the shape of a capsule, which is water-soluble at the pH, at which the hydrogen peroxide solution is stable, that is, at a pH of 4 to about 5, yet does not flocculate or precipitate in neutral solution, that is, at a pH of about 7.3.

It is, moreover, advantageous if the capsule is provided with one or two or optionally even more laser perforations, through which the auxiliary materials are released on contact with the hydrogen peroxide solution, the capsule dissolving completely when a pH of about 7 is reached in order to release the catalyst then.

The catalyst may also be present as an enzyme prill which, together with the auxiliary materials, is filled into the capsule, which has the aforementioned dissolving properties.

The catalyst-containing neutralizing agent may also be fashioned as a coated tablet, from which, with delayed dissolution of the coating, first of all the auxiliary materials are set free to change the pH of the hydrogen peroxide solution and then, at a pH of about 7, the catalyst is set free.

Furthermore suitable for the catalyst-containing neutralizing agent is a two-layer tablet, one of the layers of which, comprising soluble salts, serves to neutralize the hydrogen peroxide solution and the other layer of which contains the catalyst, it being possible to release either the auxiliary materials or the catalyst first.

The neutralizing agent may also be present as a basic gel in a coating, which is soluble at a pH of 7. The catalyst may also be present as a viscous solution in a coating, which surrounds the auxiliary materials.

Moreover, the neutralizing agent may have a semipermeable membrane as coating, through which the water to dissolve the auxiliaries penetrates into the interior and out of which the dissolved salts reach the outside due to osmotic pressure. For this purpose, the semipermeable membrane may have a perforation or it may be destroyed by osmotic pressure, whereby then the auxiliary materials and the catalyst are set free. The catalyst may be present here as an enveloped enzyme product.

Moreover, a two-layer system with a soluble and a semipermeable membrane is suitable for the time-displaced release of the auxiliary materials and the catalyst. An insoluble membrane system could be exchanged on renewed use.

A suitable two-layer system may be constructed so that the catalyst is enveloped by the semipermeable membrane, at the outside of which the auxiliary materials lie. A coating, water soluble at the pH (less than 4) of the stable hydrogen peroxide solution, moreover envelops the auxiliary materials and the semipermeable membrane enclosing the catalyst.

The decomposition of the hydrogen peroxide can be detected by a color indicator. In this connection, it is a question of the addition of a pH-redox indicator, which does not penetrate into the soft hydrophilic contact lenses and which is physiologically safe. The color indicator may also be so designed, that it is colored at pH 7 in the presence of hydrogen peroxide and colorless at pH 7 in the absence of hydrogen peroxide.

The container, in which the contact lens care or treatment is carried out, may have facilities for venting, for example, in the form of a Bunsen valve or the like, through which the oxygen released during the neutralization and decomposition of the hydrogen peroxide can escape.

The attached Figures serve to explain the invention further.

FIG. 6 shows the timewise course of the treatment of a contact lens with an example of the operation of the contact lens care set.

Figure 1:
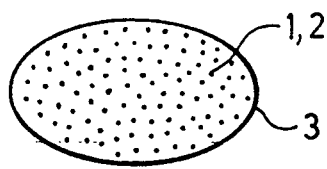
FIGS. 1 to 5 show different examples of the systems containing hydrogen peroxide and the decomposition catalyst.

In the example shown in FIG. 1, the auxiliary materials 1 and a hydrogen peroxide-splitting catalyst 2, for example in the form of catalase, are randomly distributed in the outer casing 3. The outer casing 3 may be water soluble or semipermeable after it has been acted upon for a certain period of time by the hydrogen peroxide, which has a sterilizing effect in contact lens care on the contact lens to be treated. The thickness of the casing controls the length of time (up to four hours) that the hydrogen peroxide acts on the lens, before sufficient catalase and auxiliary materials are released by the dissolution of the outer casing 3 or by the semipermeability of this casing, so that the sterilizing hydrogen peroxide is neutralized and eliminated by catalytic decomposition. In this example of the operation, the auxiliary materials and the catalyst may be released simultaneously.

Figure 2:
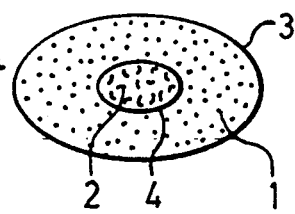

It the example shown in FIG. 2, the auxiliary materials 1 are released first, as a result of which then sterilizing hydrogen peroxide solution is neutralized. After, this, the hydrogen peroxide-destroying catalyst 2, for example in the form of catalase, comes to be used. For this purpose, the outer casing 3 is provided which, after the hydrogen peroxide has acted for a certain period of time, is soluble or which is appropriately semipermeable and which surrounds the auxiliary materials 1. The auxiliary materials 1 surround the catalyst 2, which, for its part, is surrounded by an internal casing 4, which may also be constructed so as to be soluble or semipermeable.

Figure 3:
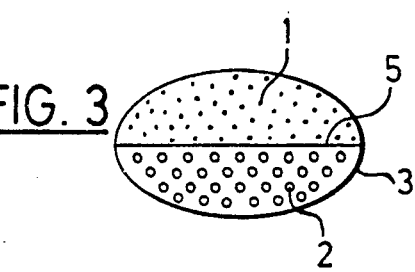

In the example shown in FIG. 3, the catalyst 2 and the auxiliary materials 1 are next to each other and are surrounded by a common outer casing 3, which is water soluble or semipermeable. In this case, the auxiliary materials 1 and the catalyst 2 may be separated by a partition 5.

Figure 4:
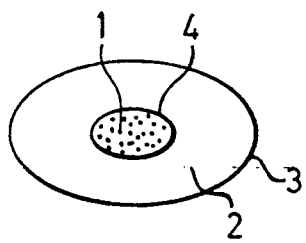

In the example shown in FIG. 4, the catalyst 2, which may be present in the form of a viscous solution, is released first, after which the auxiliary materials 1 are released. The catalyst 2 is surrounded here by the outer casing 3 and the auxiliary materials 1 by the inner casing 4. In this version, the auxiliary materials 1 lie on the inside and are surrounded by the catalyst 2.

Figure 5:
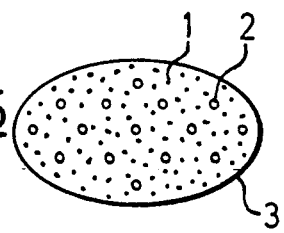

In the example shown in FIG. 5, the catalyst 2, as catalyst prill, and the auxiliary materials 1 are randomly distributed in the outer casing 3, which may be soluble or semipermeable.

FIG. 6 graphically shows the timewise course of the treatment of the contact lens with the hydrogen peroxide and the subsequent destruction of the hydrogen peroxide, after it has acted for the desired time $t_1$. The length of time that the hydrogen peroxide acts can be fixed, for example, by the thickness of the coating or by an appropriate selection of the material of the coating. The hydrogen peroxide content is plotted on the ordinate, the initial hydrogen peroxide content essentially remaining constant untill the end of the time of action $t_1$. After the release of the auxiliaries and/or the catalyst, the hydrogen peroxide content in the treatment container decreases rapidly.

Figure 7:
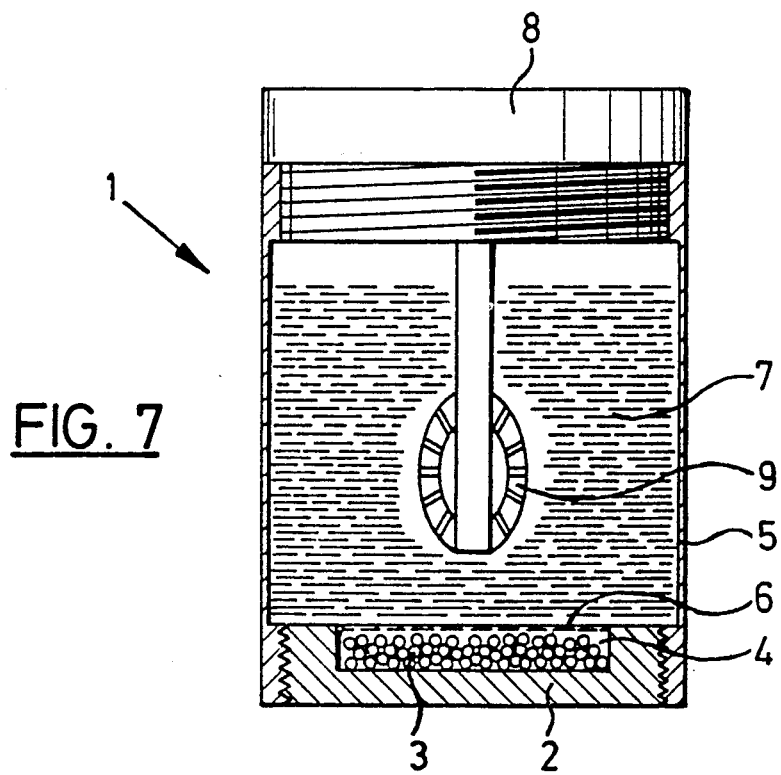
FIG. 7 shows a treatment container in side view.
Figure 8:
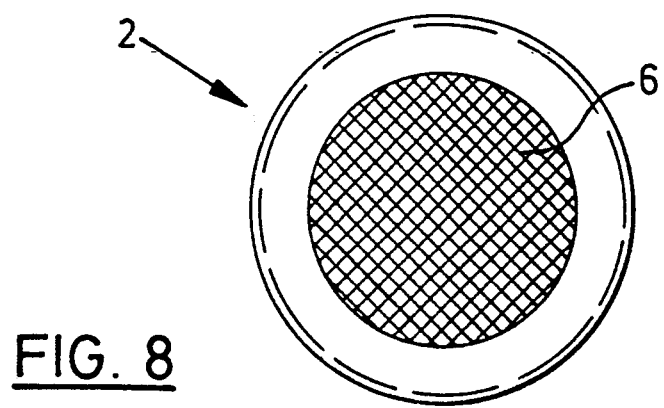
FIG. 8 shows a plan view of a container part, which can be screwed onto the treatment container and which contains particulate carrier substance, to which an enzymatic, hydrogen peroxide-decomposing catalyst is bound.

FIGS. 7 and 8 schematically shown an example of the operation of a treatment container 1, in which in a bottom part 2 particulate carrier substances 3, on which an enzymatic hydrogen peroxide-decomposing catalyst is immobilized, are disposed in a recess 4 of the bottom part 2. The bottom part 2 may, for example, may be attached by a screw thread to the treatment vessel part 5, as described, for example, in the German Offenlegungsschrift 3,410,400. The carrier substance 3, coated with the catalyst, are separated from the interior 7 of the container by means of an inert sieve netting 6, which is impermeable to the treatment solution present in the interior 7 of the container. The color of the lid 8, which is also screwed on and to which the cups 9 for the contact lenses to be treated are attached, as shown in the German Offenlegungsschrift 3,410,400, may be different from the color of screwed-on base part 2, so that the danger of confusion is precluded.

It will be understood that the specification and examples are illustrative but not limitative of the present invention and that other embodiments within the spirit and scope of the invention will suggest themselves to those skilled in the art.

A further example for a tablet, the coating of which leads to a retarded release of catalase of 30 to 60 minutes, is as follows (The composition is given, for a single tablet, in milligrams per tablet):

| Core: | Catalase powder (freeze dried) | 0.6 |
|---|---|---|
| | Mannitol | 24.4 |
| | Dextran 40 | 28.5 |
| | Dibasic Potassium Phosphate | 5.0 |
| | Polyethylene Glycol 6000 | 1.5 |
| Coating: | Hydroxypropylmethylcellulose Phthalate | 4.32 |
| | Triacetin | 0.48 |

What is claimed is:

1. A method for disinfecting a contact lens which comprises immersing the lens in an aqueous solution of $H_2O_2$, the $H_2O_2$ being present in sufficient concentration to substantially sterilize the lens, and adding to the solution, before the $H_2O_2$ has substantially sterilized the lens, a tablet comprising catalase and a polymeric coating which dissolves gradually in the aqueous solution of $H_2O_2$, said polymeric coating effecting release of the catalase which is retarded for at least 30 minutes after the addition of said tablet to the aqueous $H_2O_2$ solution, wherein the polymeric coating contains a polymer selected from the group consisting of hydroxypropylmethylcellulose phthalate polymer, a polymer from methacrylic acid or methacrylate esters, a copolymer from methacrylic acid and methacrylate esters and a copolymer from methyl vinyl ether and maleic anhydride, wherein the polymeric coating additionally contains triacetin for further control of the release of the catalase, whereby the lens so treated is suitable for application to the eye of a human without diluting the solution obtained after the catalase has decomposed any residual $H_2O_2$, or without rinsing the lens.

2. The method according to claim 1, wherein the polymer coating contains hydroxypropylmethylcellulose phthalate polymer.

3. The method according to claim 1, wherein the polymer coating consists of 70% or more of hydroxypropylmethylcellulose phthalate and up to 30% of triacetin.

4. The method according to claim 1 wherein the tablet further comprises auxiliary materials selected from the group consisting of hexitol, dextran, an alkali metal phosphate and polyethylene glycol.

5. The method according to claim 1, wherein the core of the tablet consists of catalase, mannitol, dextran having an average molecular weight of 40,000, dibasic potassium phosphate, and polyethylene glycol having an average molecular weight of 6,000, which is coated with a film consisting of hydroxypropylmethylcellulose phthalate polymer and triacetin.

6. The method according to claim 1 wherein the tablet additionally contains a color indicator to detect the decomposition of $H_2O_2$.

7. The method of claim 1 wherein the $H_2O_2$ concentration is at least 1.0%.

8. The method of claim 1 wherein the $H_2O_2$ concentration is at least 1.5%.

9. The method of claim 1 wherein the $H_2O_2$ concentration is at least 2.0%.

10. A tablet which comprises catalase and a polymeric coating comprising a polymer selected from the group consisting of hydroxypropylmethylcellulose phthalate polymer, a polymer from methacrylic acid or methacrylate esters, a copolymer from methacrylic acid and methacrylate esters and a copolymer from methyl vinyl ether and maleic anhydride, wherein the polymeric coating additionally contains triacetin, the polymeric coating effecting release of the catalase which is retarded for at least 30 minutes after the addition of said tablet to an aqueous solution of $H_2O_2$ which contains sufficient $H_2O_2$ to sterilize a contact lens.

11. A contact lens care set comprising an aqueous solution containing a sterilizing effective amount of $H_2O_2$ and a neutralizing agent in the form of a tablet, said tablet comprising catalase and a polymeric coating comprising a polymer selected from the group consisting of hydroxypropylmethylcellulose phthalate polymer, a polymer from methacrylic acid or methacrylate esters, a copolymer from methacrylic acid and methacrylate esters and a copolymer from methyl vinyl ether and maleic anhydride, wherein the polymeric coating additionally contains triacetin, the polymeric coating effecting release of the catalase which is retarded for at least 30 minutes after the addition of said tablet to the aqueous solution.

* * * * *